United States Patent [19]

Korwin et al.

[11] 4,449,645
[45] May 22, 1984

[54] DENTAL CONTAINER AND AMALGAM DISPENSING METHOD

[76] Inventors: Paul Korwin, 150-09 77th Ave., Flushing, N.Y. 11367; Robert Korwin, 3400 Red Lion Rd., Philadelphia, Pa. 19113

[21] Appl. No.: 273,914

[22] Filed: Jun. 15, 1981

[51] Int. Cl.³ .............................................. A61C 5/06
[52] U.S. Cl. ....................................... 222/49; 222/136; 222/386.5; 222/390; 604/89; 604/224
[58] Field of Search ............... 222/136, 137, 256, 390, 222/49, 386, 386.5; 128/218 M; 206/221; 604/224 (U.S. only), 89, 91

[56] References Cited

U.S. PATENT DOCUMENTS

| | | | |
|---|---|---|---|
| 1,784,260 | 12/1930 | Walstrom | 222/256 |
| 2,558,998 | 7/1951 | Yearout | 222/49 |
| 3,070,094 | 12/1962 | Sarnoff et al. | 206/221 X |
| 3,477,431 | 11/1969 | Walecka | 206/221 X |
| 3,595,439 | 7/1971 | Newby et al. | 222/386 X |
| 3,885,710 | 5/1975 | Cohen | 206/221 X |
| 4,312,343 | 1/1982 | Leveen et al. | 604/224 X |

*Primary Examiner*—Joseph J. Rolla
*Assistant Examiner*—Frederick R. Handren
*Attorney, Agent, or Firm*—Kirschstein, Kirschstein, Ottinger & Israel

[57] ABSTRACT

A dental container receives and separately stores mercury and silver ingredients until they are subsequently brought together and mixed within the container for making a ready-to-use amalgam which is directly injected from the container into a prepared tooth cavity. Visual indicators are provided on the container to advise a dental operator of the current status of the dental container.

14 Claims, 9 Drawing Figures

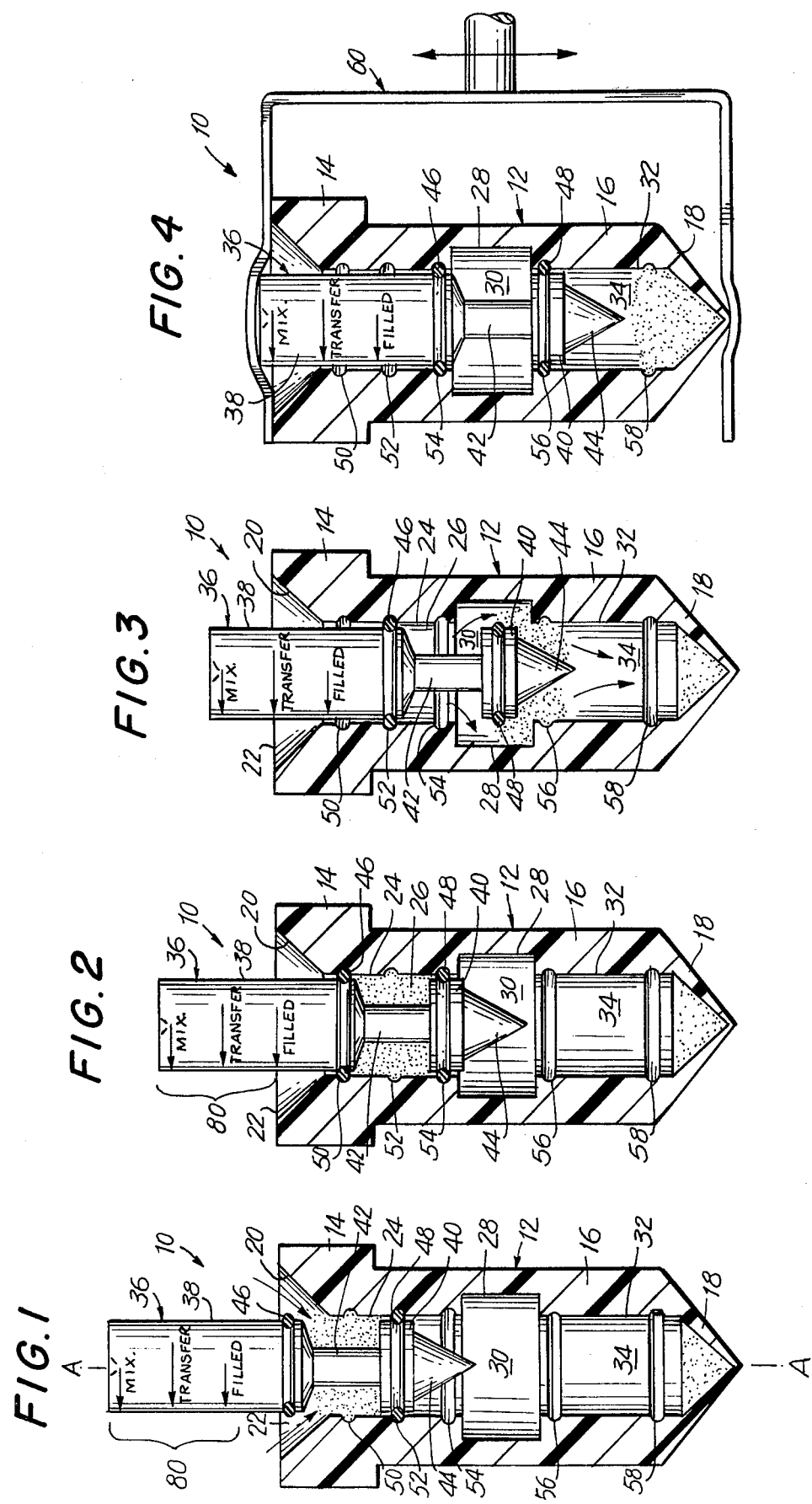

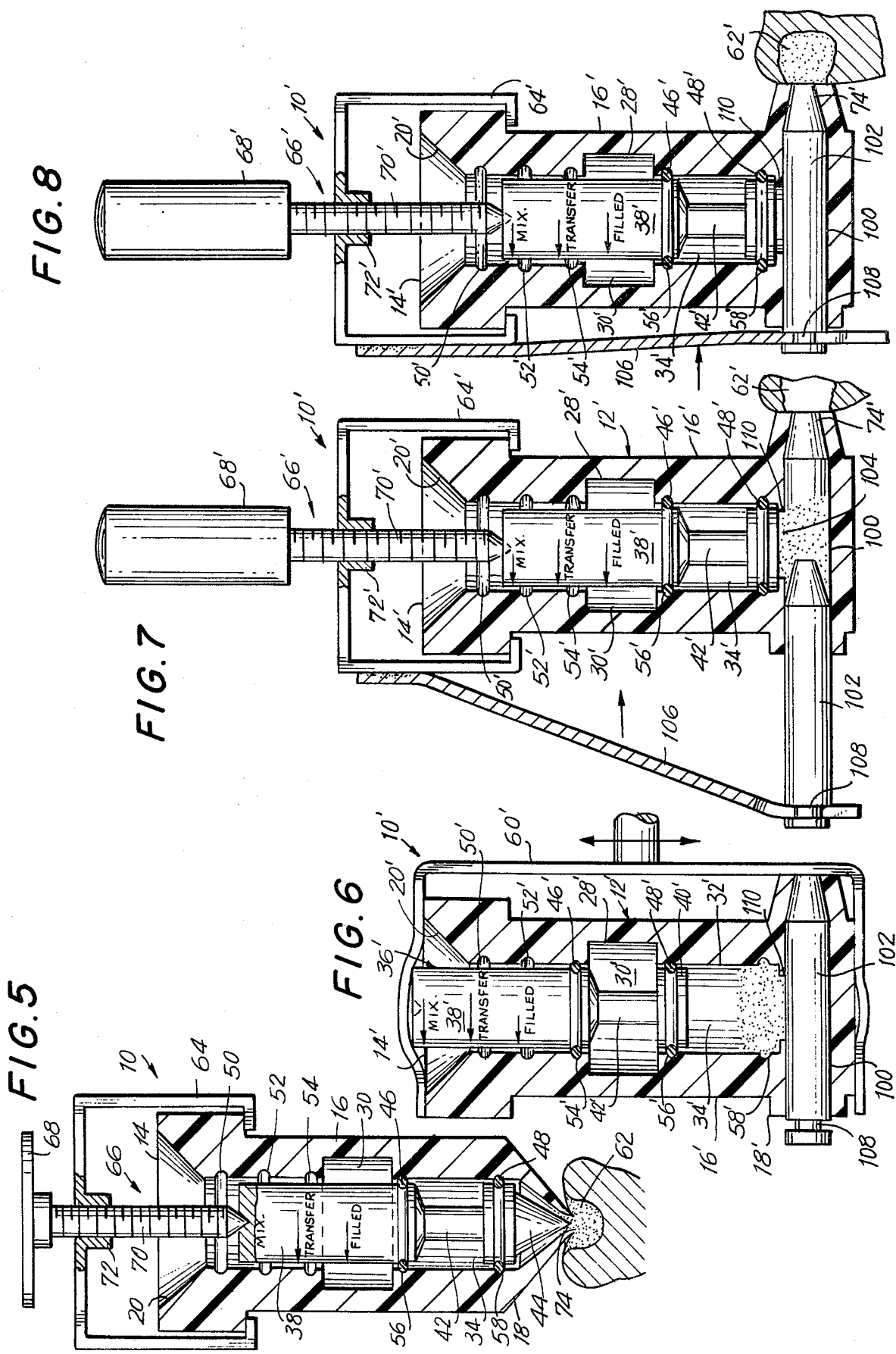

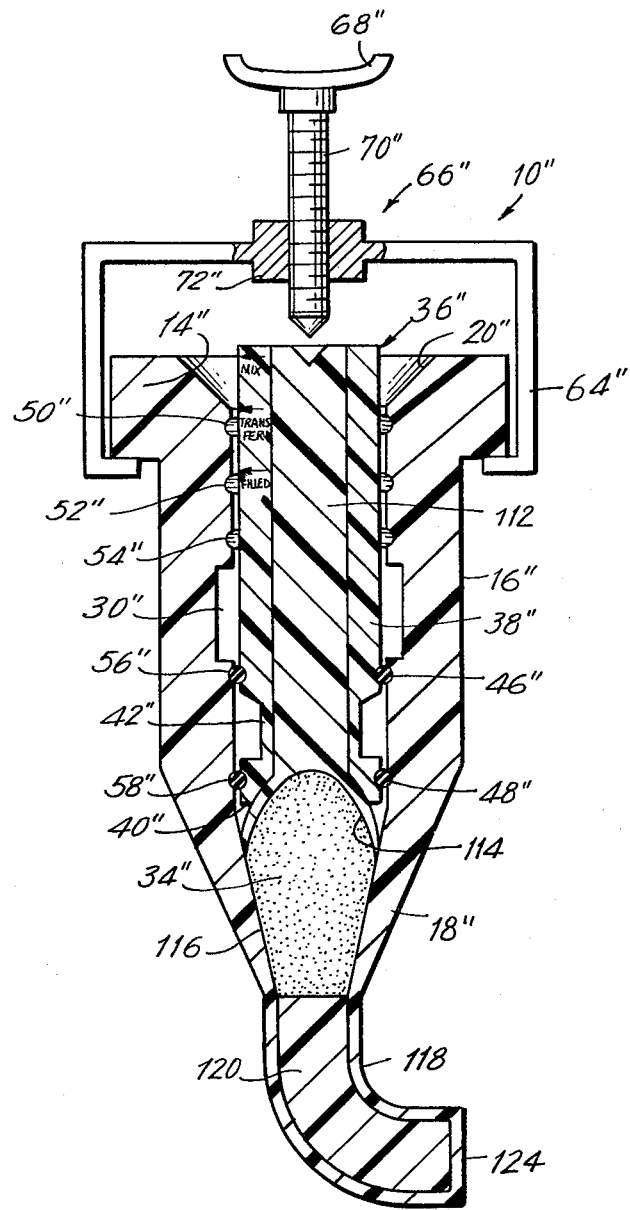

DENTAL CONTAINER AND AMALGAM DISPENSING METHOD

BACKGROUND OF THE INVENTION

1. Field of the Invention

This invention generally relates to dental containers and, more particularly, relates to small dental containers having multiple compartments for separately storing, transporting and subsequently amalgamating at least two dental preparation ingredients for making a prepared ready-to-use amalgam. Still further, this invention relates to a method of dispensing the amalgam directly into a tooth cavity.

2. Description of the Prior Art

Dental containers which separately store dental preparation ingredients until the latter are subsequently brought together and mixed to make dental preparations are well known. See, for example, U.S. Pat. Nos. 3,357,545; 3,595,439; 3,684,136; 3,731,853; 3,739,947; 3,809,225; and 3,831,742.

Numerous problems have been encountered in using the conventional containers of the prior art. One problem is to reliably seal the mercury in the container so that the mercury vapor will not be exposed to the open air and contaminate the environment. The problem of mercury contamination extends not only to the dental operator, but also to the patient. However, the prior art seals have not proven to be altogether satisfactory in preventing such contamination.

Furthermore, some prior art containers use a plunger to rupture a membrane located between the two dental preparation ingredients prior to mixing. In some instances, severed pieces of the membrane fall into and become mixed with the ingredients. This is highly undesirable, because it is very difficult to remove the severed membrane pieces from the amalgam.

Still another problem associated with the prior art is that the dental operator is not advised as to the current status of the container, i.e. whether the ingredients are currently being stored separately, or are in the process of being transferred into each other's presence, or are being mixed. This information would be of great value to the dental operator.

Yet another problem associated with the prior art containers is that the rapidly-setting amalgam mixture frequently clogs the discharge port of the container, and therefore requires the user to exert a considerable amount of muscular effort to move the plunger to discharge the amalgam. The amount of effort required frequently leads to destruction of the container itself and the scraping out of its contents, which again leads to the aforementioned problem of mercury contamination of the dental environment.

SUMMARY OF THE INVENTION

1. Objects of the Invention

Accordingly, it is the general object of this invention to overcome the drawbacks of the prior art.

It is another object of this invention to advise the dental operator of the current status of a dental container.

It is still another object of this invention to facilitate the discharging of the amalgam without requiring an excessive amount of muscular effort.

It is yet another object of this invention to reliably prevent mercury vapor and particle contamination of the dental environment resulting from the present use of open amalgam containers and special carriers used to transport the amalgam to the cavity.

An additional object of this invention is to prevent clogging of the discharge port of the amalgam container or carrier.

Still another object of this invention is to prevent contamination of the amalgam with undesired severed pieces of a ruptured membrane.

It is another object of this invention to provide a container from which the operator can transfer amalgam directly into a cavity of a tooth, without first transferring the amalgam into an open dental well and then from the well by a special carrier into a tooth cavity.

Another object of this invention is to eliminate the opening and closing of the presently used containers or capsules required during the removal of the amalgam.

Still another object is to eliminate vaporization of the mercury from the liquid state and/or the amalgam state into the air during the opening of the capsule; to eliminate spillage of the mercury; and to provide a reliable sealing of the remaining excess of the amalgam in the capsule until its safe disposal.

Yet another object is to provide an easy-to-manufacture and inexpensive dental container which is easy to operate.

An additional object of this invention is to provide a method of dispensing amalgams by directly filling dental cavities even though located in hard-to-reach places.

2. Features of the Invention

In keeping with these objects and others which will become apparent hereinafter, one feature of the invention resides, briefly stated, in a dental container for receiving and separately storing at least two dental preparation ingredients, e.g. silver and mercury, until they are subsequently brought together and mixed within the container.

In accordance with the method of this invention, a dental preparation or amalgam is made within the container and is directly injected into a tooth cavity.

The container comprises a housing having a longitudinal axis, a filler opening at one end region of the housing, a discharge port at the opposite end region of the housing, and interior wall portions which bound an interior multi-compartment chamber. The chamber extends longitudinaly intermediate the filler opening and the discharge port. The chamber has a first storage compartment in which the mercury, for example, is initially receivable, a second storage compartment in which the silver, for example, is receivable, and a transfer compartment intermediate the storage compartments.

A longitudinally-extending plunger is mounted within the chamber for longitudinal movement therealong. The plunger has a main shaft portion, an auxiliary shaft portion spaced longitudinally from the latter, and a reduced cross-section connecting shaft portion located intermediate the main and auxiliary shaft portions.

First and second sealing means, e.g. O-ring seals, are respectively mounted on the main and auxiliary shaft portions for joint movement therewith.

The plunger is manually movable by a dental operator in direction longitudinally of the chamber among a filled position, a transfer position and a mix position. In the filled position, the first and second seals sealingly engage longitudinally spaced-apart wall portions of the chamber to thereby define in the circumambient region of the connecting shaft portion the first storage compartment wherein the mercury is sealingly contained prior to mixing. In the transfer position, the second seal is disengaged from the wall portions bounding the first storage compartment, and the first and second storage compartments communicate with each other via the transfer compartment. This permits transfer of the mercury through the transfer compartment, and thereupon to the second storage compartment. In the mix position, the second seal sealingly engages wall portions of the chamber which are longitudinally spaced from the discharge port to define therebetween the second storage compartment wherein both ingredients are sealingly contained during mixing.

After mixing of the silver and mercury in a vibratory device such as an amalgamator, an openable closure means at the discharge port permits discharge of the mixed ingredients directly into a tooth cavity. The mixed ingredients can be dispensed in the direction of the movement of the plunger, or in a direction perpendicular thereto, to accommodate hard-to-reach dental cavities.

In further accordance with this invention, indicator means are provided on the container for visually indicating the plunger positions to the dental operator. This feature advises the dental operator of the current status of the container.

In accordance with the method of this invention, the method of dispensing the amalgam, as recited herein, speeds up the overall procedure and prevents premature setting of the amalgam. This method wastes less of the operator's time and eliminates several steps required to place the amalgam in the prepared cavity.

This method also eliminates spillages which frequently occur during amalgam transfer from the dental well to the hand-held amalgam carrier, and from the amalgam carrier to the tooth, and so prevents waste.

A further advantage of this invention is that the parts which are in contact with the patient are disposable, and therefore prevent patient cross-contamination by infectious organisms. The carriers used in the prior art are difficult to disinfect.

In consequence, this invention makes possible the treatment of patients with infectious diseases.

Still further, this invention permits the placement of fillings in the teeth without the assistance of other persons.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a part sectional view of an embodiment of a dental container in its charging position in accordance with this invention.

FIG. 2 is an analogous view of the FIG. 1 container in its filled position;

FIG. 3 is an analogous view of the FIG. 1 container in its transfer position;

FIG. 4 is an analogous view of the FIG. 1 container in its mix position;

FIG. 5 is an analogous view of the FIG. 1 container in its dispensing position;

FIG. 6 is a view analogous to FIG. 4, but of another embodiment of a dental container in its mix position in accordance with this invention;

FIG. 7 is a view of the FIG. 6 container in its loaded position;

FIG. 8 is a view of the FIG. 6 container in its discharge position; and

FIG. 9 is a view analogous to FIG. 4, but of still another embodiment of a dental container in its mix position in accordance with this invention.

DETAILED DESCRIPTION OF THE PREFERRED EMBODIMENTS

Referring now to the drawings, FIGS. 1-5 illustrate various operative positions of one embodiment of a dental container 10; FIGS. 6-8 illustrate various operative positions of another embodiment 10'; and FIG. 9 illustrates an operative position of still another embodiment 10". All of the embodiments depict a dental container for receiving and separately storing at least two dental preparation ingredients until they are subsequently brought together and mixed within the container. The dental container is used in accordance with the method of this invention for making a ready-to-use dental preparation which is injected directly by a dental operator from the container into a cavity or surface loss formed in a tooth.

For dental preparation ingredients, the most common ingredients in current use are mercury-silver amalgams, composite resin fillings, zinc oxide cements, and other dental cements. These fillings typically contain a liquid ingredient and a powder ingredient, or a liquid and a liquid ingredient, or a liquid and a paste ingredient, or a paste and a paste ingredient. For an amalgam filling, the liquid is typically mercury, and the powder is any dental alloy. Silver is a commonly used dental alloy ingredient. As used in this specification, the term silver is intended to be synonymous with any such dental alloy. The present invention will be discussed in connection with a mercury-silver amalgam merely for the sake of simplicity of description. It will be expressly understood that other dental preparation ingredients such as tin, copper, zinc and alloys thereof in combination with silver and mercury could also be used without departing in any way from the spirit of this invention.

Turning now to FIG. 1, the dental container 10 comprises a housing 12 elongated along a longitudinal axis A—A. The housing 12 includes an upper cylindrical portion 14, an intermediate cylindrical body portion 16, and a lower generally conically-shaped portion 18, all of one-piece construction.

An interior multi-compartment chamber is formed by interior wall portions within the housing. At the upper end region of the chamber, tapered wall portions 20 which converge in direction towards the lower portion 18 bound a tapered filler opening 22 through which the dental ingredients pass to charge the container. Generally cylindrical wall portions 24 form the outer circumferential surface of a first storage compartment 26 (see FIG. 2) in which one of the dental ingredients, e.g. the mercury, is initially receivable and storable. Generally cylindrical wall portions 28 bound a transfer compartment 30. Generally cylindrical wall portions 32 form the outer circumferential surface of a second storage compartment 34 in which the other of the dental ingredients, e.g. the silver, is receivable and storable. The filler opening 22, the first storage compartment 26, the transfer compartment 30, and the second storage compartment 34 are successively arranged lengthwise along the container and together form a bore therein. The diameter of the first and second storage compartments are approximately, but need not be, the same; and the diameter of the transfer compartment is larger than the diameter of the storage compartments.

A longitudinally-extending plunger 36 is mounted within the chamber for longitudinal movement therealong. The plunger 36 comprises an upper land or main shaft portion 38 at one end region thereof, a lower land or auxiliary shaft portion 40 longitudinally spaced from the main shaft portion, an intermediate connecting shaft portion 42 located between the main and auxiliary portions, and a tip portion 44 at the opposite end of the plunger. The main and auxiliary shaft portions 38, 40 are cylindrical and have a diameter which is slightly less than the diameter of the storage compartments 26, 34 so as to permit the shaft portions 38, 40 to tightly and slidably fit therein with a slight clearance. The connecting shaft portion 42 is of reduced cross-section and has a diameter less than the diameter of the main and auxiliary shaft portions. The tip portion 44 has a conical shape, with its apex at the leading end of the plunger. The tapered tip portion 44 is sharp and is constituted of a rigid material which is of sufficient strength to rupture the lower housing portion 18 to form a discharge port as described below. The main, connecting and auxiliary shaft portions and the tip portion are of one-piece construction, and move jointly along the longitudinal axis.

A first resilient sealing means or O-ring rubber seal 46 is securely fixed in an annular recess formed in the main shaft portion 38. A second resilient sealing means or O-ring rubber seal 48 is securely fixed in another annular recess formed in the auxiliary shaft portion 40. The seals 46, 48 are located on opposite axial ends of the connecting shaft portion 42, and are operative for resiliently and sealingly bearing against the interior wall portions of the chamber.

A plurality of annular grooves 50, 52, 54, 56, and 58 are formed in, and are longitudinally spaced apart along, the interior wall portions of the chamber for detentively receiving at least one of the O-ring seals 46, 48 in each of various operative positions of plunger 36. Grooves 50, 52, and 54 are formed in wall portion 24; and grooves 56 and 58 are formed in wall portion 32.

In response to manually exerting pressure on the plunger 36, the plunger 36 is moved in longitudinal direction among a charging position (FIG. 1), a filled position (FIG. 2), a transfer position (FIG. 3), a mix position (FIG. 4), and a dispensing position (FIG. 5). Prior to moving the plunger 36 to the illustrated charging position, a premeasured amount of silver powder is admitted into the second storage compartment 34. In the illustrated charging position, the liquid mercury is admitted past the filler opening 22 in the direction of the illustrated arrows into the circumambient region of the connecting shaft portion 42. The seal 48 detentively engages groove 52 and prevents any liquid mercury from entering the second storage compartment 34 at this time.

Once a premeasured amount of liquid mercury has been admitted into the circumambient region of the connecting shaft portion 42, the plunger 36 is manually moved to the filled position in which the seals 46, 48 detentively engage grooves 50 and 54, respectively. The seals 46, 48 resiliently and sealingly engage the grooves 50, 54 and define therebetween in the circumambient region of the connecting shaft portion 42 the first storage compartment 26. The seal 46 prevents the mercury and its vapor from escaping the container and contaminating the exterior environment. The seal 48 prevents the mercury from reacting with the silver powder at this time. In the filled position, both the silver and the mercury are separately stored even for long periods of time. The container can be shipped or transported in safety without accidental undesired movement of the plunger 36 due to the secure engagement of the seals 46, 48 with their associated grooves 50, 54.

Once the dental operator decides to make the dental preparation, the plunger 36 is thereupon moved to the transfer position in which the seal 48 is moved into the transfer compartment 30, thereby breaking the sealing engagement of the seal 48 with the groove 54. This places the first and second storage compartments 26, 34 in communication with each other via the transfer compartment 30. The liquid mercury now flows with assistance from gravity from the first compartment 26 into the transfer compartment 30, and thereupon into the second storage compartment 34. The mercury bypasses the seal 48 through the annular clearance formed by the smaller diameter seal 48 and the larger diameter wall portions 28. The seal 46 now detentively engages the groove 52 and prevents any mercury contamination of the exterior environment.

Once the transfer is completed, the plunger is again manually moved until the seal 46 engages the groove 54, and the seal 48 engages the groove 56, both of which define the mix position. The seals 46, 48 both serve to prevent contamination of the exterior environment at this time, and both serve to sealingly contain the two ingredients in the second storage compartment 34 during the mixing step.

The container is now placed in any suitable mixing apparatus. In the dental field, vibratory mixers or amalgamators adapted to hold dental containers of the type and miniature dimensions described herein are available. Amalgamator 60 diagrammatically represents such a conventional device which shakes the dental container very rapidly to effect homogeneous mixing of the silver and the mercury to form the amalgam.

After the container is removed from the amalgamator 60, the amalgam is now ready to be directly injected from the container into a tooth cavity 62. As depicted in FIG. 5, to assist in discharging the amalgam from the second storage compartment into the cavity 62, a manually-operable actuator means 66 is mounted on the housing 10 above the upper portion 14 thereof. The actuator means 66 comprises a mounting clip mounted with snap-type action on the upper support portion 14 of the housing, and a rotary member mounted on the mounting clip 64 for turning movement relative thereto. The rotary member has a handle portion 68 and a threaded shaft portion 70 which threadedly engages a threaded passage formed in a central flange 72 on the clip 64. As the handle 68 is turned, the threaded shaft 70 axially advances. The leading end of the shaft 70 bears against the trailing end of the plunger 36 in force-transmitting relationship therewith so as to axially move the plunger past the mix position. The leading end of shaft 70 is preferably conically-shaped and fits within a corresponding recess of complementary contour in the trailing end of the main shaft portion 38 so as to maintain the shaft 70 in force-transmitting engagement with the plunger 36 during the axial movement.

In the dispensing position of FIG. 5, the rotary member 68, 70 has been turned so as to move the plunger 36 so that seals 46, 48 detentively engage grooves 56, 58, respectively. In this position, the sharp tip portion 44 of the plunger has punctured the lowest end of the lower housing portion 18 so as to form a discharge port 74, i.e. the ruptured lower housing portion constitutes an openable closure means. The amalgam is discharged through the port 74 directly into the tooth cavity 62. The tip portion 44 is tapered and diverges in direction away from the leading end of the plunger, so that the discharge port increases in dimension as the plunger is moved through the ruptured port. The ever-increasing size of the discharge port prevents clogging of the amalgam thereat. The plunger can be moved beyond the illustrated dispensing position to discharge substantially all of the amalgam as desired.

In further accordance with the invention, indicator means 80 are provided on the main shaft portion 38 for visually indicating at least some of the aforementioned plunger positions to a dental operator to indicate the operative condition of the container at any given moment. The indicator means 80 includes the legends "filled," "transfer," and "mix" and respectively-associated arrows to respectively denote the aforementioned filled, transfer and mix positions. The arrows associated with each legend are arranged on the main shaft portion, such that each respective arrow is aligned with the top of the container housing when each respective plunger position has been reached. By sighting along the top of the container housing and observing the legend and arrow thereat, the dental operator is advised of the current container status.

The aforementioned grooves 50, 52, 54, 56, and 58 which detentively receive at least one of the seals 46, 48 in each plunger position cooperate with the indicator means 80 to advise the dental operator of the current plunger position. Whereas the indicator means provides a "visual" indication of the current plunger position, the detent action of the seals and the grooves provides a "manual feel" or sensory indication of the current plunger position. The dental operator can tell that the plunger has been advanced the requisite axial distance by manually sensing the lock-type action of the seals as they are being received in their associated grooves.

Turning now to FIGS. 6-8, the modified container 10' is essentially identical to container 10, except in the structure for and method of dispensing the mixed ingredients. The amalgam in container 10 is dispensed axially, i.e. in the direction of movement of the plunger 36, whereas the amalgam in container 10' is dispensed radially, i.e. perpendicularly to the direction of movement of the plunger 36. This transverse discharge of the amalgam grants the dental operator more freedom of movement in filling hard-to-reach cavities in the mouth.

The housing 12' is essentially identical to housing 12, except for the lower portion 18' which bounds a transverse passage 100 in which a pusher member 102 is slidably mounted for displacement therealong. The plunger 36' is essentially identical to plunger 36, except for the tip portion 44 which has been eliminated, because this modified embodiment does not involve rupturing any portion of the housing. The discharge port 74' is already formed at the axial end of the transverse passage 100. Other parts of the housing 12', plunger 36' and actuator means 66' which are analogous to parts of the housing 12, plunger 36 and actuator means 66 have been identified by primed numerals, and have not been described for the sake of brevity.

In the mix position of the plunger shown in FIG. 6, the cylindrical pusher member 102 extends across the lower opening 104 of the second storage compartment 34' to block the opening 104 and prevent the mixed ingredients in the compartment 34' from escaping therefrom. Prior to reaching the mix position, the operation of the dental container 10' is as described earlier for container 10.

After mixing has been completed, the mixed ingredients are dispensed by operation of the manually-operable actuator means 66' that is mounted on the support portion 14' of the container. The actuator means 66' is essentially identical to actuator means 66, except for the different shape of the handle 68', and except for the biasing means or leaf spring 106. One end of the spring 106 is permanently mounted on the mounting clip 64', and its opposite end is detachably hooked over the reduced cylindrical neck portion 108 at one end of the cylindrical pusher member 102. The spring 106 has an inclined intermediate offset portion located between its ends. The spring 106 has a relaxed condition which, as shown in FIG. 7, manually biases the pusher member 102 to a loading position in which the pusher member does not extend across the opening 104, thereby unblocking the same. Hence, the actuating means 66' is operative for advancing the plunger 36' to the loading position of FIG. 7 to thereby push the mixed ingredients past the opening 104 and into the transverse passage 100 in front of the pusher member 102. An annular ledge 110 is formed at the region between the second storage compartment 34' and the transverse passage 100, and is operative for abutting with the axial end face of the auxiliary shaft portion 40'. This abutment prevents undesired entry of plunger 36' into the passage 100.

In order to discharge the amalgam in front of the pusher member 102, the dental operator exerts manual pressure on the spring 106 in the direction of the illustrated arrow to urge the pusher member 102 transversely through the passage towards the discharge position of FIG. 8. The amalgam is dispensed out of the discharge port 74' and directly into the tooth cavity 62'. In the discharge position, the offset portion of the spring 106 is more in alignment with its end portions, and the spring is under an increased tension. Once manual pressure on the spring 106 is released, the spring returns to its relaxed position shown in FIG. 7.

Turning now to FIG. 9, the container 10" is essentially identical to the container 10, except that the lower housing portion 18" has been modified to radially dispense the amalgam, and the plunger 36" has been modified to include a central piston 112 having a concavely-shaped head 114 of resiliently yieldable material. Parts of the container 10" analogous to parts of the container 10 have been identified by double-primed materials, and have not been described for the sake of brevity.

The lower housing portion 18" has inwardly tapered wall portions 116 which bound a generally conical shape for the second storage compartment 34". The lower housing portion 18" has a circular hook-shaped extension 118 which extends over an arc length of at least 90°, and preferably more. A plug 120 is mounted in the hollow interior of the extension 118 to prevent minor portions of the mixed ingredients from entering the narrow confines of the extension 118 and not being mixed with the main body of the amalgam. The 90° curvature of the hooked extension 118 permits the dental operator to dispense the amalgam in a perpendicular direction to the direction of advancement of the plunger 36", and allows the operator easy access to hard-to-reach cavities.

The plunger 36" is essentially the same as plunger 36, except that rather than having a solid interior, a longitudinal passage is formed therethrough to slidably accommodate the piston 112. The central piston 112 and the outer shell of the plunger 36" are jointly movable in response to manual pressure to assume the aforementioned plunger positions. However, once having reached the mix position, it is the central piston 112, and not the outer shell of the plunger 36", which is axially advanced further downwardly by the actuator means 66" to eject the mixed ingredients.

Prior to ejecting the amalgam, the far end region 124 of the extension 118 is sheared to form a discharge port through which the plug 120 followed by the amalgam can pass. The actuator means 66" is operative to axially advance the piston 112 so that its concavely-shaped head 114 resiliently and sealingly bears against the tapered wall portions 116. The resilient nature of the edges of the head 114 together with the inwardly tapered wall portions 116, cooperate to urge the mixed ingredients in the compartment 34" towards the discharge port under a pressure force whose magnitude increases as the central piston 112 is moved towards the discharge port. In other words, the amalgam is being forced through a space which is gradually decreasing in cross-section. This feature increases the force being exerted on the amalgam within the compartment 34" and minimizes the amount of manual effort required to urge the amalgam outwardly of the discharge port. Also, this feature serves to prevent clogging of the amalgam in the hook extension.

In terms of suitable materials, the housing can be constituted of metal or plastic material, and preferably transparent plastic material so as to permit better viewing of the indicator means. The plungers, pistons, and pusher members can likewise be made of plastic or metal material. The O-ring seals are preferably made of rubber.

It will be understood that each of the elements described above, or two or more together, may also find a useful application in other types of constructions differing from the types described above.

While the invention has been illustrated and described as embodied in a dental container and amalgam dispensing method, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

1. A dental container for receiving and separately storing at least two dental preparation ingredients until they are subsequently brought together and mixed within the container, for making a settable, semi-solid dental preparation ready for use, said container comprising:

(a) a housing having a longitudinal axis, a filler opening at one end region of the housing, a discharge port at the opposite end region of the housing, a discharge port at the opposite end region of the housing, and interior wall portions bounding an interior multi-compartment chamber which extends longitudinally intermediate the filler opening and the discharge port, said chamber having a first storage compartment in which one of the ingredients is initially receivable, a second storage compartment in which the other of the ingredients is receivable, and a transfer compartment intermediate the storage compartments;

(b) a longitudinally-extending plunger mounted within the chamber for londitudinal movement therealong, said plunger having a main shaft portion, an auxiliary shaft portion spaced londitudinally from the main shaft portion, and a reduced cross-section connecting shaft portion intermediate the main and auxiliary shaft portions;

(c) first and second sealing means respectively mounted on the main and auxiliary shaft portions for joint movement therewith;

(d) said plunger being manually movable in direction longitudinally of the chamber among
  (1) a filled position in which the first and second sealing means sealingly engage longitudinally spaced-apart wall portions of the chamber to thereby define in the circumambient region of the connecting shaft portion the first storage compartment wherein said one ingredient is sealingly contained prior to mixing,
  (2) a transfer position in which the second sealing means is disengaged from the wall portions bounding the first storage compartment, and in which the first and second storage compartments communicate with each other via the transfer compartment, to thereby permit transfer of said one ingredient through the transfer compartment and thereupon to the second storage compartment, and
  (3) a mix position in which the second sealing means sealingly engages wall portions of the chamber which are longitudinally spaced from the discharge port to define therebetween the second storage compartment wherein both ingredients are sealingly contained during mixing;

(e) openable closure means at the discharge port for permitting discharge of the mixed ingredients upon opening of the closure means;

(f) indicator means displayed on the plunger for visually indicating each of said filled, transfer and mix plunger positions to a dental operator; and (g) tactile sensory means for manually detecting each of said filled, transfer and mix plunger positions by the dental operator, said tactile sensory means including a plurality of grooves formed in the interior wall portions of the chamber for receiving at least one of the sealing means with snap-in locking action in each of said filled, transfer and mix plunger positions, said first and second sealing means being received in a first and a second groove in the filled position, said first sealing means being received in a third groove in the transfer position, and said first and second sealing means being received in the second and a fourth groove in the mix position, whereby the dental operator is simultaneously visually and tactilely advised of each of said plunger positions.

2. The dental container of claim 1, wherein said discharge port is of one-piece with the housing and is constituted of rupturable material, and wherein said plunger has a tip portion at the leading end thereof, said tip portion being constituted of material of sufficient strength to rupture the discharge port when the plunger is moved past the mix position.

3. The dental container of claim 2, wherein said tip portion is tapered and diverges in direction away from the leading end of the plunger so that the opening at the ruptured port increases in dimension as the plunger is moved through the ruptured port.

4. The dental container of claim 1, wherein said shaft portions have a generally cylindrical configuration, and wherein said compartments have a generally circular cross-section.

5. The dental container of claim 1, wherein the filler opening is tapered and converges in direction towards the discharge port to facilitate charging of the ingredients into the chamber.

6. The dental container of claim 1, wherein the first and second sealing means constitute a pair of O-ring seals which resiliently bear against the wall portions of the chamber.

7. The dental container of claim 1, wherein said indicator means is located on the main shaft portion, and separately alphabetically indicates the filled, transfer and mix positions.

8. The dental container of claim 1, wherein said housing has a support portion; and further comprising manually-operable actuator means including a mounting clip mounted on the support portion, and a rotary member mounted on the mounting clip for turning movement relative thereto, said rotary member being in force-transmitting relationship with the plunger to move the same when the rotary member is turned.

9. The dental container of claim 1; and further comprising means for dispensing the mixed ingredients in a direction transversely of the longitudinal axis, said dispensing means including a transverse passage extending transversely of the chamber, and a transversely-extending pusher member mounted in the transverse passage for displacement in a direction transverse to the longitudinal axis, said dispensing means also including pusher means for displacing the pusher member among a blocking position in which the pusher member extends across the chamber and prevents communication between the latter and the transverse passage to thereby prevent entry of the mixed ingredients therein, a loading position in which the pusher member does not extend across the chamber and permits communication between the latter and the transverse passage to thereby permit the mixed ingredients to be loaded therein, and a discharge position in which the pusher member discharges the loaded ingredients outwardly of the transverse passage.

10. The dental container of claim 9, wherein said dispensing means further includes biasing means for normally urging the pusher member to said loading position.

11. The dental container of claim 1, wherein said second storage compartment is tapered and converges in longitudinal direction towards the discharge port, and wherein said plunger includes a central piston mounted for longitudinal movement within the plunger, said central piston having a concavely-shaped head constituted of resiliently yieldable material, and operative for resiliently bearing against the wall portions bounding the tapered compartment to thereby urge the mixed ingredients therein towards the discharge port under a pressure force whose magnitude increases as the central piston is moved towards the discharge port.

12. The dental container of claim 1, wherein the discharge port has a circular curved shape which extends over an arc length of at least 90°.

13. The dental container of claim 9, wherein the discharge port is located at an end of the transverse passage, and wherein the pusher member extends to the discharge port in the discharge position.

14. The dental container of claim 1, wherein the discharge port has an enlarged, flow-through cross-section to avoid clogging of the settable, semi-solid dental preparation during discharge.

* * * * *